United States Patent [19]
Mizutani et al.

[11] Patent Number: 5,445,627
[45] Date of Patent: Aug. 29, 1995

[54] SANITARY NAPKIN

[75] Inventors: Satoshi Mizutani; Masahiro Kashiwagi, both of Kawanoe, Japan

[73] Assignee: Uni-Charm Corporation, Ehime, Japan

[21] Appl. No.: 285,470

[22] Filed: Aug. 3, 1994

[30] Foreign Application Priority Data

Aug. 6, 1993 [JP] Japan .................. 5-043336 U

[51] Int. Cl.[6] .............................................. A61F 13/15
[52] U.S. Cl. .................. 604/385.2; 604/387; 604/389; 604/390
[58] Field of Search .............. 604/385.1–387, 604/389–396, 365–366; 602/54–56

[56] References Cited

U.S. PATENT DOCUMENTS

| 2,512,713 | 6/1950 | Cahill | 604/387 |
| 2,742,903 | 4/1956 | Lightner | 604/387 |
| 4,596,246 | 6/1986 | Jackson | 604/389 |
| 4,753,648 | 6/1988 | Jackson | 604/389 |
| 5,304,160 | 4/1994 | Igaue et al. | |

FOREIGN PATENT DOCUMENTS

| 0330206 | 8/1989 | European Pat. Off. . |
| 0426235 | 5/1991 | European Pat. Off. . |
| 0508477 | 10/1992 | European Pat. Off. . |
| 5-7222 | 2/1993 | Japan . |
| 2233235 | 1/1991 | United Kingdom ............ 604/385.1 |

Primary Examiner—Randall L. Green
Assistant Examiner—K. M. Reichle
Attorney, Agent, or Firm—Lowe, Price, LeBlanc & Becker

[57] ABSTRACT

A sanitary napkin characterized by that there are provided adjacent transversely opposite side edges of a basic body a pair of elastically stretchable flaps in the form of straps and rising from a backsheet, adhesives being applied on top surface of said flaps so that said flaps may be adhesively fastened to the user's skin.

3 Claims, 2 Drawing Sheets

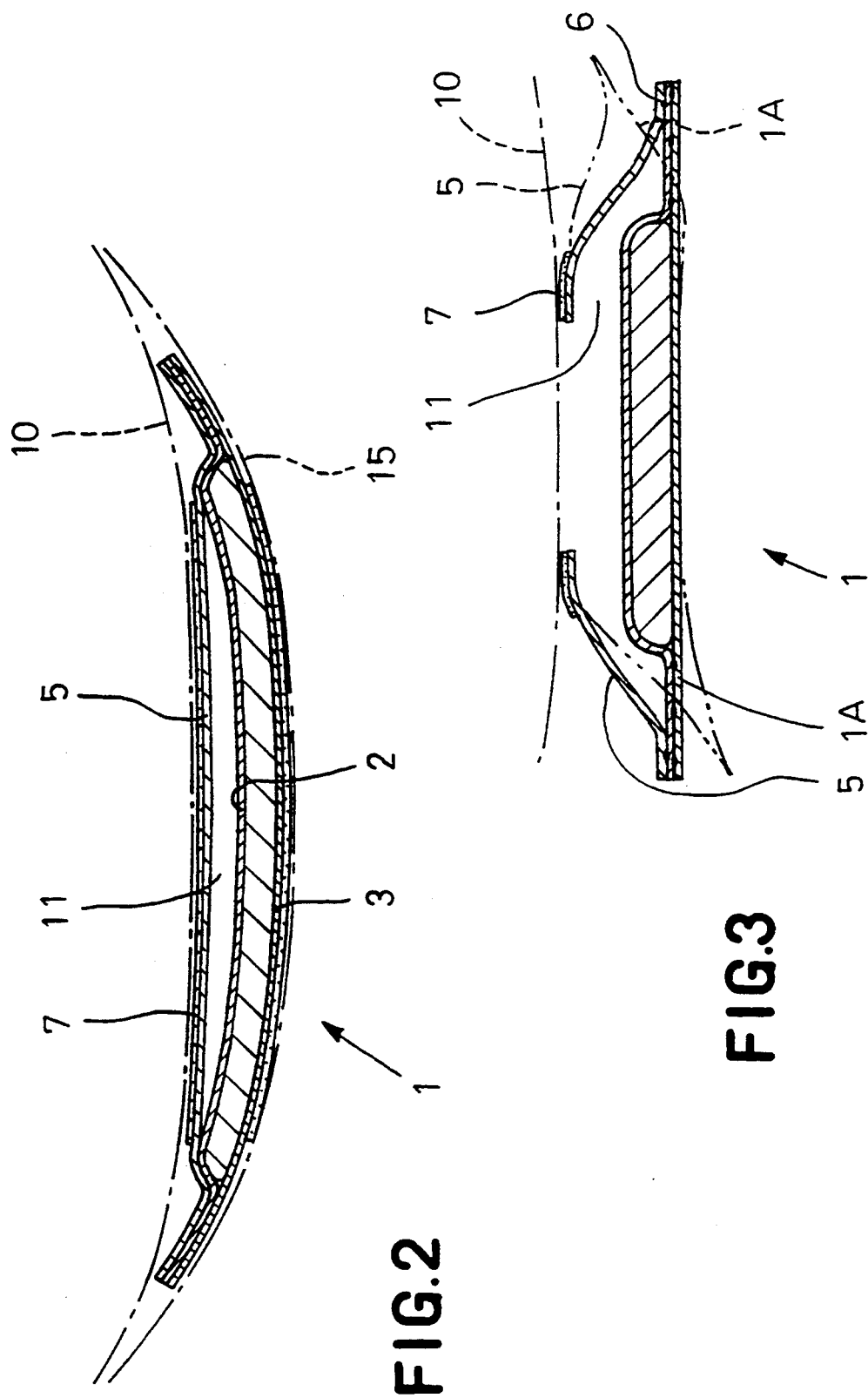

SANITARY NAPKIN

BACKGROUND OF THE INVENTION

This invention relates to a sanitary napkin for use by women during menstrual periods for absorbing an retaining menstrual fluids.

It is well known in sanitary napkins to apply a skin-contacting surface thereof with suitable adhesives so that the skin-contacting surface may be adhesively fastened to the user's skin and thereby otherwise possible leakage of menstrual fluids due to the displacement of the napkin during its use may be avoided. For example, Japanese Utility Model Application Disclosure No. 1993-7222 discloses a sanitary napkin provided along transversely opposite sides thereof with fastening means comprising band-like hydrophobic cushion members made of foamed a urethane or the like and adhesives applied on top surfaces thereof. As an alternative measure to avoid said leakage of menstrual fluids, it is also known to provide transversely opposite sides of a napkin with flaps so that these flaps may cooperate with a topsheet to form a pocket and any quantity of menstrual fluids tending to flow transversely of the napkin may be reliably received by the pocket.

The adhesion of the adhesives employed must be necessarily enhanced in order to assure that said fastening means of prior art might compensate for the movement of the user's body without separation of said fastening means from the user's skin. However, the enhanced adhesion would increase the user's discomfort inevitably accompanying the separation of the napkin from the user's skin. The napkin of prior art including the side flaps having rubber threads bonded thereto in their stretched state along respective free edges of the flaps is certainly advantageous in that the pocket is sufficiently opened as the napkin is longitudinally curved inward to receive menstrual fluids effectively. However, the pocket can be sufficiently opened only when the napkin is not in close contact with the user's skin i.e., the napkin is at a position appropriately spaced from the user's skin. Consequently, the conventional sanitary napkin of such type can not effectively avoid the leakage possibly occurring when the napkin gets out of its proper position longitudinally and/or transversely.

SUMMARY OF THE INVENTION

In view of the problems as described above, it is a principal object of the invention to provide a sanitary napkin so improved that there are provided adjacent transversely opposite side edges of the napkin with flaps comprising elastically stretchable straps applied on their top surfaces with adhesives and thereby the leakage of menstrual fluids can be effectively avoided even if the napkin shifts relative to the user's skin during use.

The object set forth above is achieved, according to the invention, by a sanitary napkin comprising a basic body of the napkin comprising a liquid-permeable topsheet, a liquid-resistant backsheet and a liquid-absorbent core sandwiched between said sheets, and elastically stretchable flaps longitudinally provided adjacent transversely opposite side edges of said basic body and rising from said topsheet, characterized by that said flaps comprise elastically stretchable straps bonded in their stretched state to said basic body and applied on their top surfaces with adhesives.

With the sanitary napkin constructed as described above, the elastically stretchable straps are reliably fastened to the user's skin under the effect of adhesives applied on their top surfaces so that the straps may be deformed to compensate for a shift of the basic body occurring longitudinally and/or transversely relative to the part of the user's body with which the basic body should be maintained in contact and thereby function to maintain the basic body of napkin in proper Contact with the part of the user's body so as to avoid the leakage of menstrual fluids. It will be readily understood that the straps is more freely deformed to compensate for a larger shift of the napkin and thereby to avoid the leakage of menstrual fluids more effectively so far as each of the straps is dimensioned so as to have a larger width. The flaps in the form of straps are bonded in their stretched state to the basic body, so the flaps are not wrinkled even when they contract.

BRIEF DESCRIPTION OF THE DRAWINGS

A sanitary napkin according to the invention will be described more in detail by way of example in reference with the accompanying drawings, in which:

FIG. 2 is a sectional view of said sanitary napkin as being upon the user's body, taken along a line 2—2 in FIG. 1; and FIG. 3 is a view similar to FIG. 2 taken along a line 3—3 in FIG. 1.

PREFERRED EMBODIMENTS OF THE INVENTION

Figure 1:
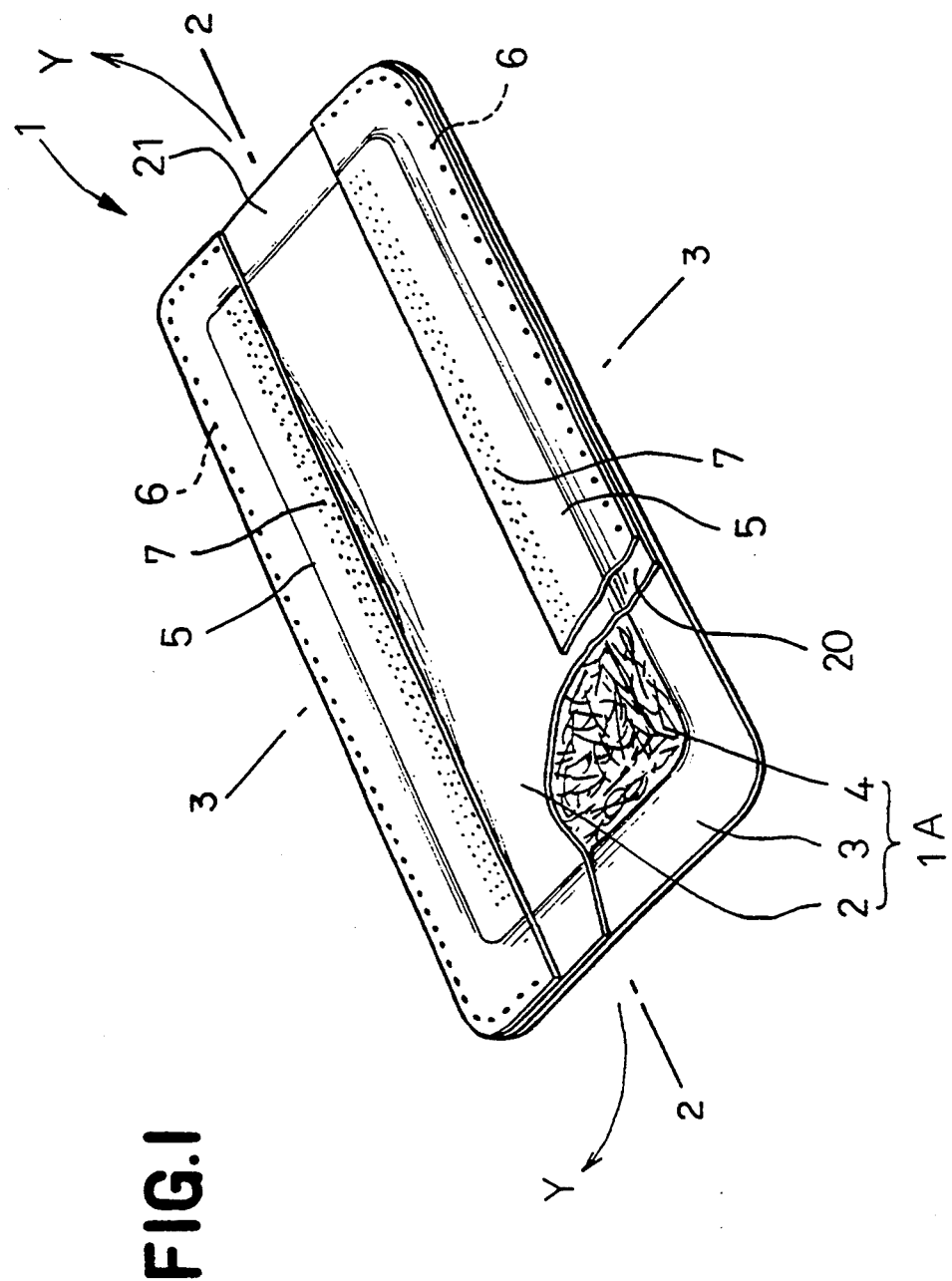
FIG. 1 is a perspective view showing, as, partially broken away, an embodiment of a sanitary napkin.

FIG. 1 is a perspective view showing, as partially broken away, an embodiment of a sanitary napkin 1 according to the invention in its flattened state. The napkin 1 comprises a basic body 1A and elastically stretchable flaps 5, the basic body 1A comprising a liquid-permeable topsheet 2 formed by a nonwoven fabric of thermoplastic synthetic fibres, a liquid-resistant backsheet 3 formed by a plastic film and a liquid-absorbent core 4 formed by a mixture of fluff pulps and high absorption polymers and sandwiched between the top- and backsheets 2, 3. Portions of the top-and backsheets 2, 3 extending outward from transversely opposite side edges and from longitudinally opposite ends of the core 4 are thermally welded together so as to form side flaps 20 and end flaps 21. The elastically stretchable flaps 5 comprise straps formed by a thermoplastic elastomer sheet, side edges and opposite ends of which are bonded along bonding lines 6 defined by hot melt type adhesives in their stretched state to the side flaps 20 and the end flaps 21, respectively. Inner side edges of these flaps 5 are free and applied on their top surfaces longitudinally with suitable pressure sensitive adhesives 7. It should be understood that the napkin prior to use has a zone applied with adhesives 7 respectively protected by a release paper (not shown) against contamination. After the removal of the release paper, the napkin 1 is inwardly curved as indicated by the line Y—Y and the flaps 5 are reliably fastened to the user's skin as the release paper is removed and then the napkin 1 is held against the proper part of user's body.

FIGS. 2 and 3 are sectional views taken along lines 2—2 and 3—3 in FIG. 1, respectively, showing the napkin 1 in its curved state, wherein imaginary lines indicate the user's skin and shorts 15. As the napkin 1 is curved as illustrated, the flaps 5 which have been in their stretched states contract except the bonded zones and at the same time tend to rise be risen from the topsheet 2. The flaps 5 may be constructed so as to remain in their states of tension even after they have contracted in order to facilitate them to be fastened to the user's skin without the formation of wrinkles. Between the flaps 5 and the topsheet 2, there is formed a pocket 11 adapted to be opened inwardly as the napkin 1 is spaced from the user's skin 10 as illustrated.

Referring to FIG. 3, two-dotted imaginary chain lines indicate, by way of example, the movement of the basic body 1A and the flaps 5. The flaps 5 made of elastomer sheet are soft and elastic enough to be movable both longitudinally and transversely relative to the basic body 1A so that, even if the basic body 1A shifts relative to the user's skin 10, the flaps 5 compensate for such shift of the basic body 1A to maintain the basic body 1A in proper contact with the user's skin 10 and thereby to avoid the leakage of menstrual fluids otherwise possibly occurring transversely of the napkin 1. The wider the width of the flap 5 is, the higher a freedom of motion of the flap 5 is and lower a force tending to separate the flap 5 off the user's skin 10 becomes. Accordingly, the adhesives 7 may be selected to have a relatively low effect of adhesion and thereby to alleviate discomfort for the user accompanying the separation of the flaps 5 off the user's skin 10. To facilitate the flaps 5 to compensate for a shift of the basic body 1A, the flaps 5 according to this specific embodiment are bonded only along their peripheral zones defined by linearly applied hot melt type adhesives 6 to the basic body 1A (see FIGS. 1 and 3).

It is also possible without departure from the scope of the invention to form the topsheet 2 from materials other than a nonwoven fabric, e.g., an open cell plastic sheet. The expression "liquid-resistant backsheet" 3 covers the sheet of every type having a liquid-permeability lower than that of the topsheet 2, e.g., a liquid-impermeable plastic sheet or an air-permeable but a liquid-impermeable sheet. The backsheet 3 may be provided on its underside with suitable fastener means used to fasten the napkin to the shorts. The elastically stretchable flaps 5 may be formed not only by the previously mentioned elastomer sheet but also by elastic nonwoven fabric or rubber sheet.

The napkin according to the invention includes, adjacent the transversely opposite side edges of the basic body, the flaps or straps made of elastically stretchable sheets having their top surfaces adapted to be adhesively fastened to the user's skin so that these flaps may be deformed to compensate for shifting of the napkin longitudinally and/or transversely relative to the user's skin and thereby reliably avoid the leakage of menstrual fluids. Furthermore, the pocket defined between the flaps and the topsheet is opened and avoids the leakage of menstrual fluids even if the napkin is downwardly moved away from the user's skin. The invention allows the pocket to be further easily opened by adhesively fastening the flaps along their free edges to the user's skin.

By dimensioning the flaps to be relatively wide, it is possible to improve a motion freedom of the flaps, on one hand, and to employ adhesives having a relatively low effect of adhesion without apprehension that the flaps might be readily separated from the user's skin. The use of such adhesive alleviates discomfort experienced by the user during the separation of the flaps.

What is claimed is:

1. A sanitary napkin comprising a basic body of the napkin comprising a liquid-permeable topsheet, a liquid-resistant backsheet and a liquid-absorbent core sandwiched between said sheets, and elastically stretchable flaps longitudinally provided adjacent transversely opposite side edges of said basic body and rising from said topsheet, characterized by that said flaps comprise elastically stretchable straps bonded in their stretched state to said basic body and applied on their top surfaces with adhesives.

2. A sanitary napkin according to claim 1, wherein a side edge and opposite ends of each of said flaps are bonded onto said topsheet.

3. A sanitary napkin according to claim 1, wherein said flaps comprise a thermoplastic elastomer sheet.

* * * * *